US011399899B2

(12) United States Patent
Bos

(10) Patent No.: US 11,399,899 B2
(45) Date of Patent: Aug. 2, 2022

(54) MODULAR ROBOTIC DEVICE FOR PRECISION SURGICAL BONE REMOVAL AND OTHER APPLICATIONS

(71) Applicant: Eindhoven Medical Robotics B.V., Eindhoven (NL)

(72) Inventor: Jordan Bos, Kerkdriel (NL)

(73) Assignee: Technische Universiteit Eindhoven, Eindhoven (NL)

( * ) Notice: Subject to any disclaimer, the term of this patent is extended or adjusted under 35 U.S.C. 154(b) by 62 days.

(21) Appl. No.: 15/770,839

(22) PCT Filed: Nov. 10, 2016

(86) PCT No.: PCT/EP2016/077243
§ 371 (c)(1),
(2) Date: Apr. 25, 2018

(87) PCT Pub. No.: WO2017/081137
PCT Pub. Date: May 18, 2017

(65) Prior Publication Data
US 2018/0318019 A1    Nov. 8, 2018

Related U.S. Application Data

(60) Provisional application No. 62/253,575, filed on Nov. 10, 2015.

(51) Int. Cl.
*B25J 9/08* (2006.01)
*A61B 34/30* (2016.01)
(Continued)

(52) U.S. Cl.
CPC .............. *A61B 34/30* (2016.02); *A61B 17/16* (2013.01); *B25J 9/046* (2013.01); *B25J 9/08* (2013.01); *B25J 9/108* (2013.01); *B25J 13/085* (2013.01); *B25J 19/0004* (2013.01); *A61B 2017/1602* (2013.01); *B25J 9/04* (2013.01); *B25J 9/1679* (2013.01)

(58) Field of Classification Search
CPC ........ B25J 9/108; B25J 17/025; B25J 9/0048; B25J 9/08; B25J 9/101; B25J 19/0004; F16C 19/362; F16C 19/54; F16C 2226/70; F16C 2226/80; A61B 5/1513
See application file for complete search history.

(56) References Cited

U.S. PATENT DOCUMENTS 2,891,829 A * 6/1959 Irvin ..................... H02K 5/1732
384/542
3,060,792 A * 10/1962 Brunson ................. G02B 27/62
356/140

(Continued)

FOREIGN PATENT DOCUMENTS

CN       104668958       6/2015
DE       102013005982   10/2014
FR              2974322 A1 * 10/2012 ............ B25J 18/007

*Primary Examiner* — Bobby Rushing, Jr.
(74) *Attorney, Agent, or Firm* — Suiter Swantz pc llo

(57) ABSTRACT

A seven-degrees of freedom modular robotic device is provided for controlling an instrument, e.g. a bone-drilling or milling device with a precision of about 50 μm and maximum force of 50 N. The robotic device is a serial kinematic chain of six rotational degrees of freedom and one translational degree of freedom.

6 Claims, 5 Drawing Sheets

(51) Int. Cl.

| | | |
|---|---|---|
| *A61B 17/16* | (2006.01) | |
| *B25J 9/10* | (2006.01) | |
| *B25J 13/08* | (2006.01) | |
| *B25J 9/04* | (2006.01) | |
| *B25J 19/00* | (2006.01) | |
| *B25J 9/16* | (2006.01) | |

(56) References Cited

U.S. PATENT DOCUMENTS

| | | | | |
|---|---|---|---|---|
| 4,664,539 | A * | 5/1987 | Li | F16C 19/55 |
| | | | | 384/102 |
| 4,697,935 | A * | 10/1987 | Yasui | F16C 29/041 |
| | | | | 384/47 |
| 5,178,031 | A * | 1/1993 | Orsi | B25J 9/1025 |
| | | | | 318/568.11 |
| 5,193,401 | A | 3/1993 | Bridges | |
| 6,014,909 | A * | 1/2000 | Fiora | B25J 15/04 |
| | | | | 74/490.02 |
| 6,568,854 | B2 * | 5/2003 | Schleinitz | E02F 9/12 |
| | | | | 384/448 |
| 7,849,761 | B2 * | 12/2010 | Forslund | B25J 17/0283 |
| | | | | 414/8 |
| 8,347,753 | B2 * | 1/2013 | Larsson | B25J 19/0029 |
| | | | | 74/490.01 |
| 8,479,893 | B2 * | 7/2013 | Nuissl | F16C 19/362 |
| | | | | 188/171 |
| 9,815,210 | B2 * | 11/2017 | Takahashi | B25J 17/02 |
| 10,035,261 | B2 * | 7/2018 | Johnson | B25J 9/126 |
| 10,335,944 | B2 * | 7/2019 | Inoue | B25J 9/102 |
| 2002/0037119 | A1 | 3/2002 | Schleinitz | |
| 2011/0019953 | A1 | 1/2011 | Nuissl et al. | |
| 2012/0011956 | A1 * | 1/2012 | Lundberg | B25J 9/04 |
| | | | | 74/490.03 |
| 2012/0020792 | A1 * | 1/2012 | Frank | F03D 7/0204 |
| | | | | 416/169 R |
| 2012/0174317 | A1 * | 7/2012 | Saracen | A61B 6/0457 |
| | | | | 5/601 |
| 2013/0081502 | A1 * | 4/2013 | Long | B25J 9/102 |
| | | | | 74/490.04 |
| 2013/0096574 | A1 * | 4/2013 | Kang | A61B 17/1622 |
| | | | | 606/130 |
| 2014/0222198 | A1 | 8/2014 | Emami et al. | |
| 2014/0222207 | A1 | 8/2014 | Bowling et al. | |
| 2014/0276952 | A1 * | 9/2014 | Hourtash | B25J 9/1638 |
| | | | | 606/130 |
| 2016/0120611 | A1 * | 5/2016 | Lohmeier | A61B 90/50 |
| | | | | 606/130 |

\* cited by examiner

MODULAR ROBOTIC DEVICE FOR PRECISION SURGICAL BONE REMOVAL AND OTHER APPLICATIONS

CROSS-REFERENCE TO RELATED APPLICATIONS

This application is a 371 of PCT application PCT/EP2016/077243 filed Nov. 10, 2016. PCT application PCT/EP2016/077243 claims the benefit of U.S. Provisional application 62/253,575 filed Nov. 10, 2015.

FIELD OF THE INVENTION

This invention relates to robotic devices. Specifically, the invention relates to medical robotics.

BACKGROUND OF THE INVENTION

Surgical precision bone removal procedures are often invasive for the patient, time consuming, exhaustive for the surgeon and with high-risks on complications since the surgeon removes bone with a razor-sharp cutter within millimeters of vital structures. An area of interest is the lateral skull base/ear region, where multiple vital structures are located. Procedures to improve or restore hearing, e.g. cochlear implantations, are invasive for the patient where a lot of excessive bone has to be removed and have a high risk on complications, e.g. loss of facial expressions, loss of hearing, loss of balance, loss of taste, etc. Surgical procedures to remove lesions in this area are often, besides having high risks and being invasive, also very time consuming and exhausting for the surgeon; drilling towards the lesion, while trying to evade all vital structures, which are all hidden in bone, with a razor-sharp cutter up to six hours long. After this drilling and milling, the tumor still has to be removed.

Designing a surgical or medical robot is a balance between compactness, precision, force output and safety. The bone drilling procedures mentioned infra require precision and a relatively high force output. The present invention advances the art by providing a medical robot specifically designed for the demands in delicate bone drilling and milling procedures.

SUMMARY OF THE INVENTION

The present invention provides a seven-degrees of freedom robotic device for controlling an instrument with a precision of more or less of 50 μm and maximum force of 50 N. Examples of instruments are a bone-drilling or milling device, a 3D printing nozzle or a laser. The robotic device is a serial kinematic chain of six rotational degrees of freedom and one translational degree of freedom. The rotational degrees of freedom are designed using six circular cross-roller bearings. Each two adjacent circular cross-roller bearings are more or less perpendicularly (90±5 degrees) aligned and connected to each other such that the six circular cross-roller bearings form a stacked serial kinematic chain arrangement. Two adjacent circular cross-roller bearings are rigidly connected to each other through a rigid connection element which connects the inner ring of the first circular cross-roller bearing to the outer ring of the second circular cross-roller bearing in the more or less perpendicularly alignment. The serial kinematic chain is extended by one or two linear cross-roller bearings adding a translation (the seventh) degree of freedom. The one or two linear cross-roller bearings are connected to the inner ring of the top/last circular cross-roller bearing in the chain of six interconnected circular cross-roller bearings. An instrument is mounted to the two linear cross-roller bearings. Each one of the rotational degrees of freedom can be constrained by a locking element thereby reducing the total number of degrees of freedom and providing flexibility and modularity to the robotic device. Force and/or torque sensors could be added to aid in the control and feedback The robotic design has several advantages, such as the:
Ability to have a compact design with seven degrees of freedom (6 rotational and 1 linear in a serial design).
Availability of a large working volume relative to size of robot suitable for wide range of procedures. For example, the robot device fits in box of 200×200×400 mm$^3$.
Ability to achieve more or less of 50 μm of accuracy at the tip of the instrument, due to high rigidity using cross roller bearings close to each other.
Ability to withstand drilling and milling forces up to 50 N at the tip of the instrument.
Ability to measure forces and torques exerted at the surgical tool.
Ability to lower the number of degrees of freedom of the robot for the desired task at the supervisor's choosing. This is accomplished by the locking option to lock every rotational degree of freedom individually.
Fact that it will not intervene with e.g. a microscope, which hangs above the surgical field.
Ability to create modular units whereby every unit represents one degree of freedom.
Fact that it is cost effective and maintenance effective due to the modular design.
Ability where one or multiple degrees of freedom can be taken over manually, by being able to decouple the output axis (inner ring of every circular cross roller bearing) from the gearbox and motor of every degree of freedom.

DETAILED DESCRIPTION

Figure 1:
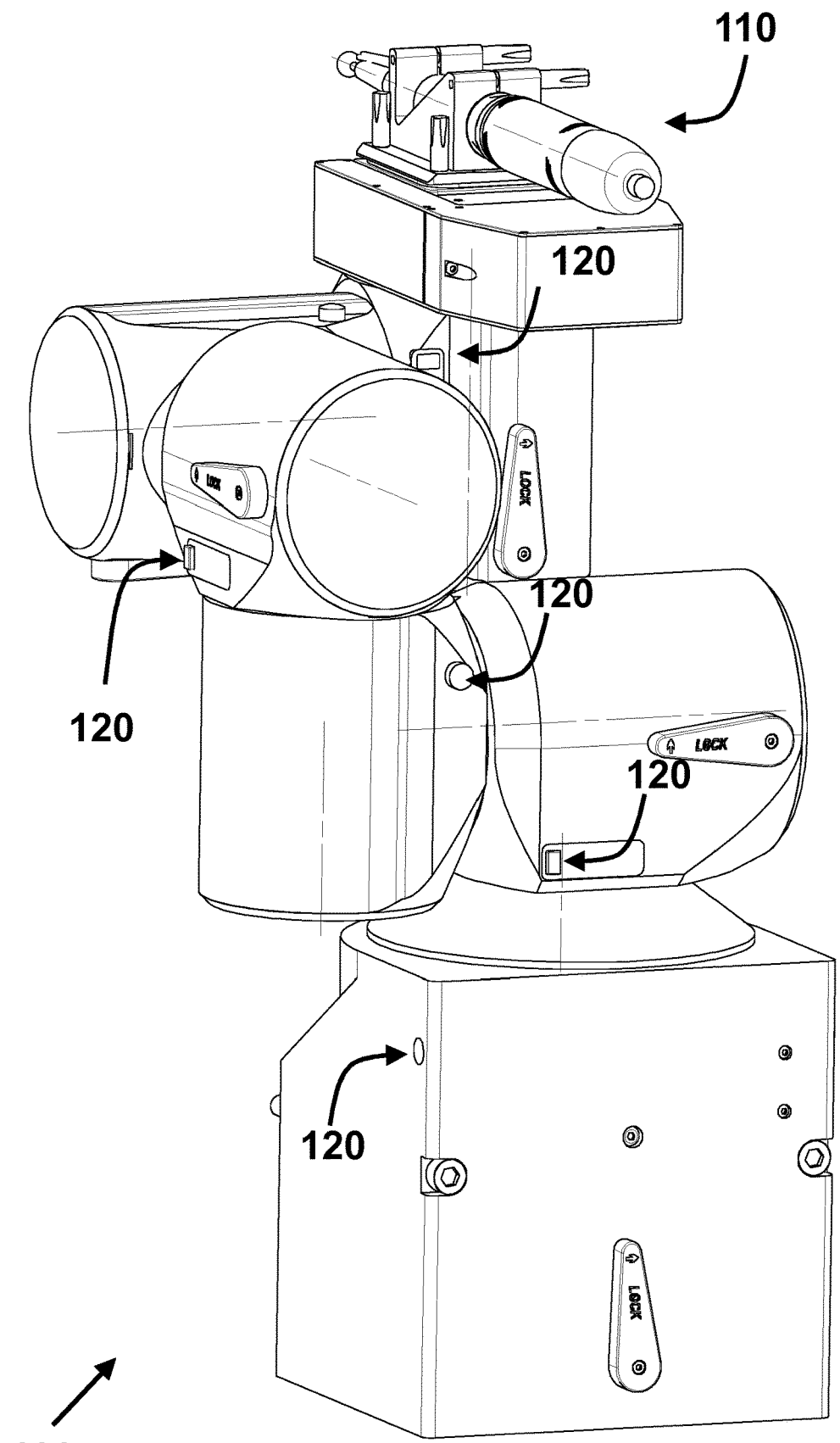
FIG. 1 shows a modular robotic device for precision surgical bone removal and other applications according to an exemplary embodiment of the invention.

The present invention provides a compact modular serial robot designed with which both relative high-precision (~50 μm) could be obtained and which can cope with high forces (maximum of 50 N) in a compact design with 7 degrees of freedom as shown in FIG. 1. In this example 6 degrees of freedom use modular building blocks. Using interchangeable modular building blocks gives the possibility to have a cost effective and serviceably effective design, while satisfying safety, performance and human-robot interaction requirements.

FIG. 1 shows an overview of modular robotic device 100 with a bone-drilling or milling device 110 for precision surgical bone removal and other precision applications. This example shows a robot with seven degrees of freedom where each of the degrees of freedom can be locked using for example individual locks when deemed necessary to change the number of degrees of freedom. Push buttons 120 would enable or disable the lock.

Figure 2:
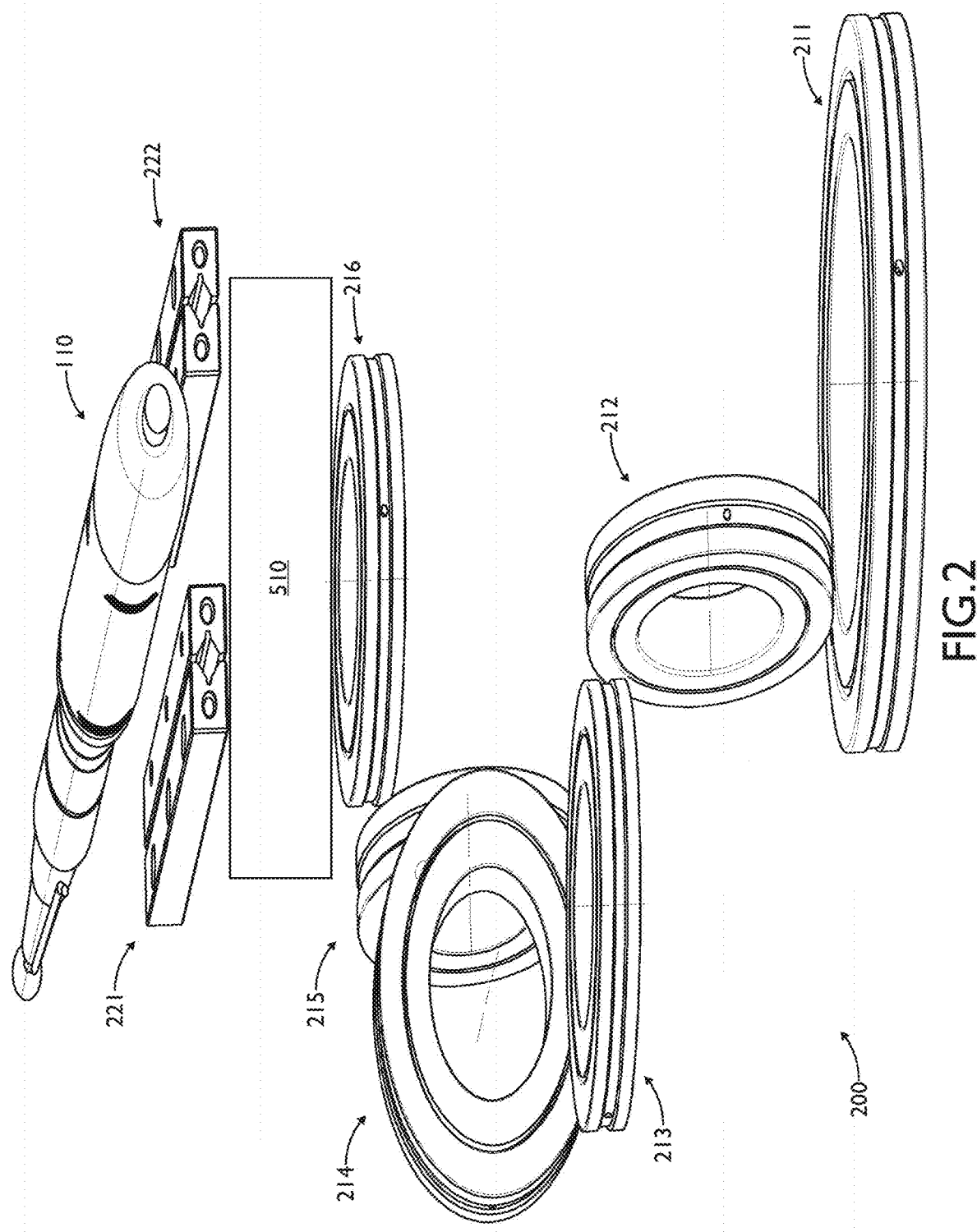
FIG. 2 shows in an exploded view and according to an exemplary embodiment of the invention the modular robotic device as in FIG. 1.

FIG. 2 shows an exploded view 200 of the modular robotic device shown in FIG. 1. Six inter-connected circular cross-roller bearings 211, 212, 213, 214, 215, 216 create six degrees of freedom. Any combination of two cross-roller bearings is connected to each other at a 90±5 degrees angle, i.e. perpendicular as shown in FIG. 2. A perpendicular connection results in the most compact and rigid connection in a robot for multiple degrees of freedom, e.g. at least five degrees of freedom. The perpendicular design aids in keeping the distance between the cross-roller bearings as small as possible resulting is the highest rigidity possible (i.e. precision) as well as a more compact design. Two linear cross-roller bearings 221, 222 create the seventh degree of freedom for controlling the bone-drilling device 110.

Figure 3:
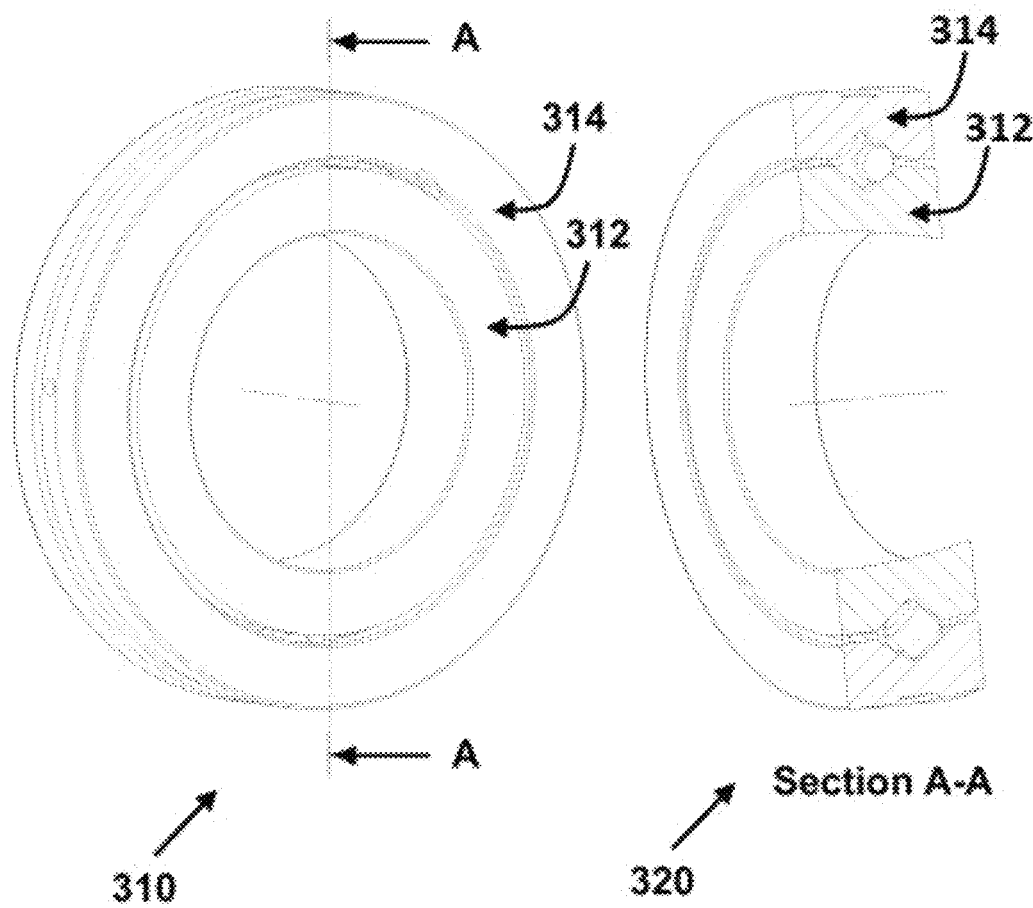
FIG. 3 shows a circular cross-roller bearing according to an exemplary embodiment of the invention.

FIG. 3 shows an example of a circular cross-roller bearing 310 and in a cross-section view A-A in 320. Bearing 310 distinguishes an inner ring 312 and an outer ring 314.

Figure 4:
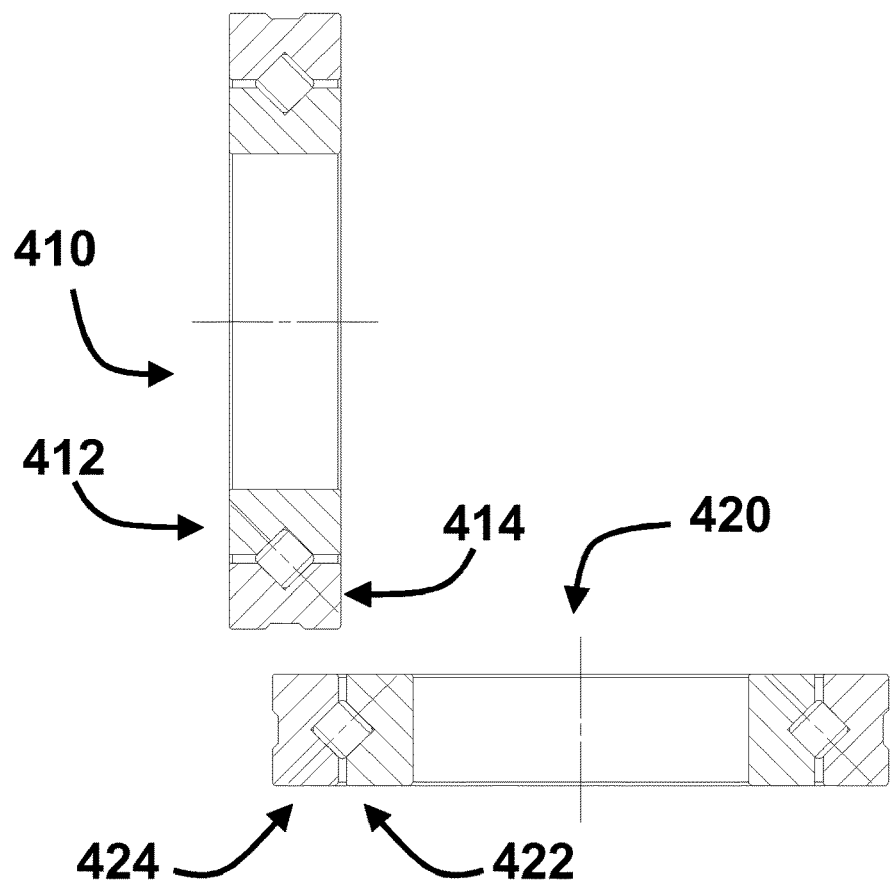
FIG. 4 shows a cross-section of two circular cross-roller bearings aligned more or less perpendicularly according to an exemplary embodiment of the invention.

FIG. 4 shows cross sections of two circular cross-roller bearings 410, 412 aligned and connected more or less perpendicularly. Circular cross-roller bearing 410 features an inner ring 412 and an outer ring 414, whereas circular cross-roller bearing 420 features an inner ring 422 and an outer ring 424.

Figure 5:
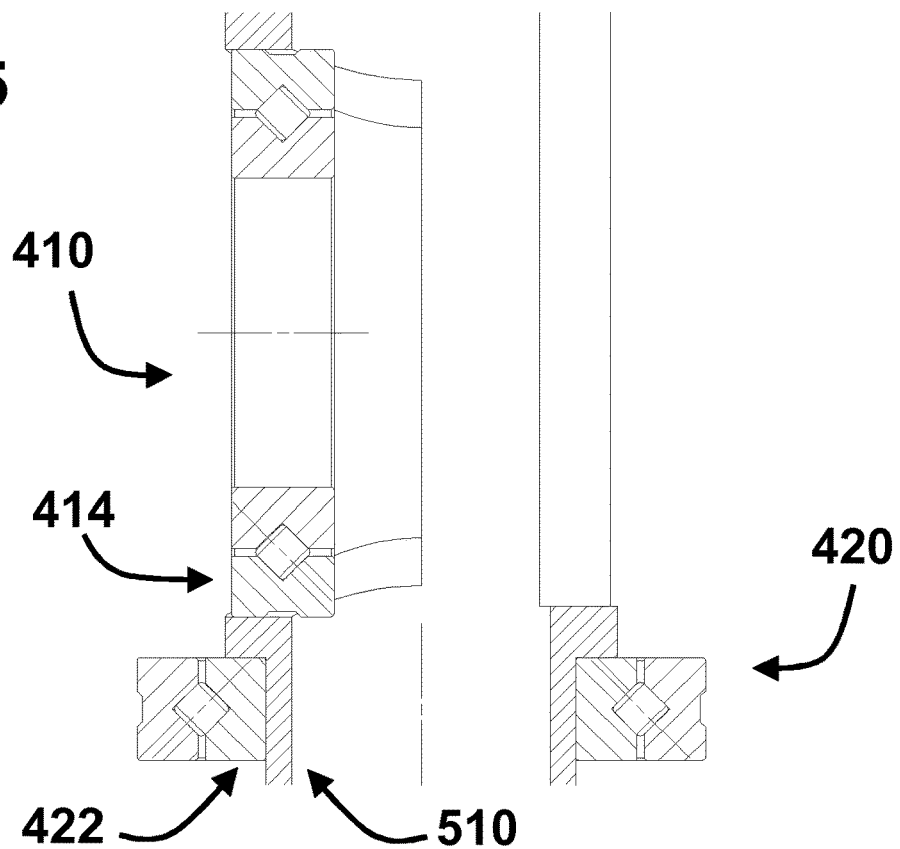
FIG. 5 shows according to an exemplary embodiment of the invention two circular cross-roller bearings 410, 420 as shown in FIG. 4.

FIG. 5 shows cross section of the two circular cross-roller bearings 410, 420 as shown in FIG. 4 with bearings 410, 420 forming a serial kinematic chain as they are connected by rigid connection element 510. Rigid connection element 510 allows bearing 410 to move with respect to bearing 420; inner ring 422 is connected to outer ring 414 via 510. Referring back to FIGS. 1 and 2, the six inter-connected circular cross-roller bearings 211, 212, 213, 214, 215, 216 are rigidly connected to each other in a similar fashion as shown in FIG. 5 creating a six (rotational) degrees of freedom serial kinematic chain. Two linear cross-roller bearings 221, 222 can be connected to cross-roller bearing 216 also in a similar fashion as shown in FIG. 2 to extend the serial kinematic chain by adding translation as the seventh degree of freedom for controlling the bone-drilling/milling device 110. Overall the serial kinematic chain is capable of controlling the bone-drilling/milling device 110 with seventh degrees of freedom.

Figure 6:
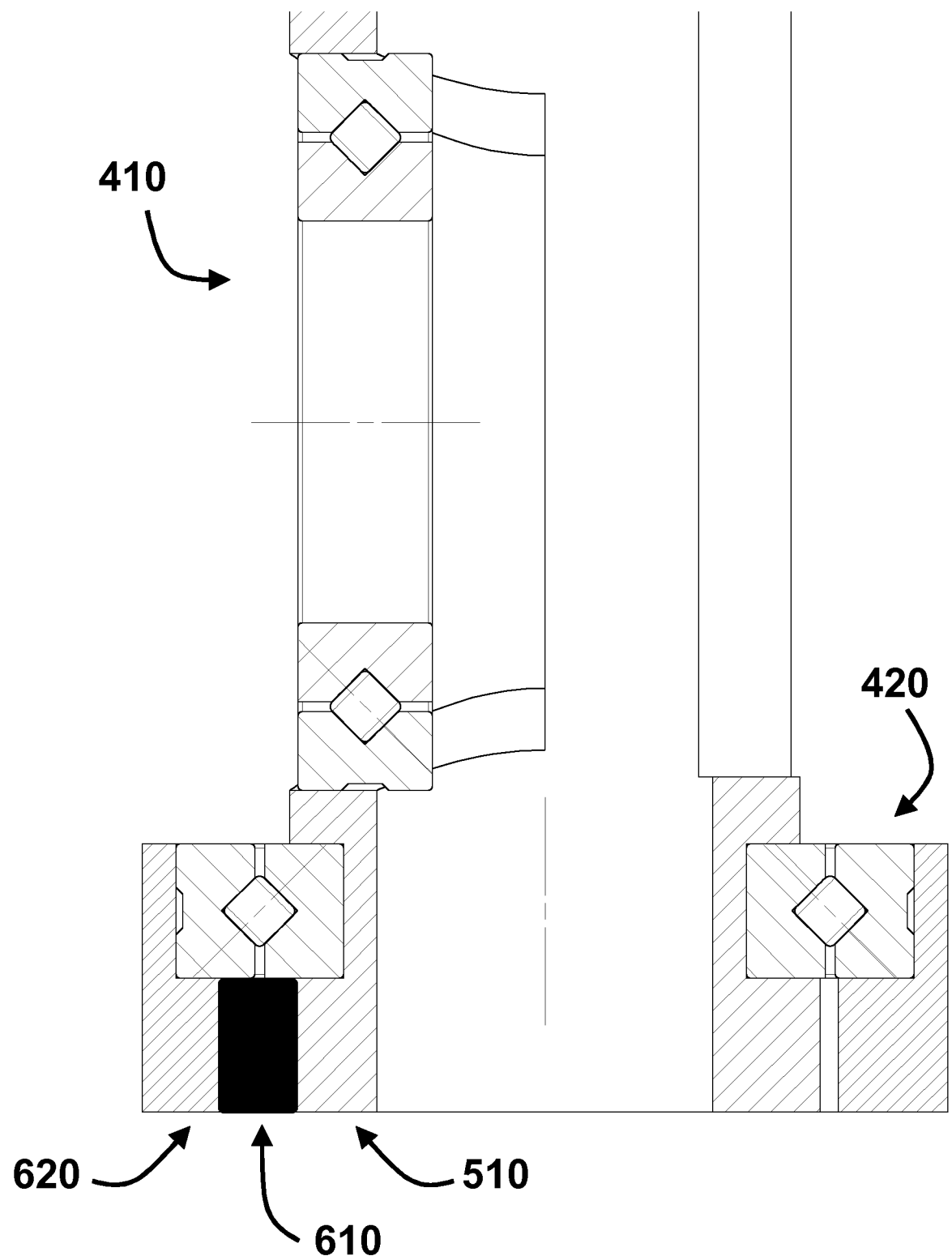
FIG. 6 shows according to an exemplary embodiment of the invention two circular cross-roller bearings as shown in FIG. 4 with bearings connected more or less perpendicularly by a rigid connection element.

To introduce flexibility and modularity of the degrees of freedom as shown in FIG. 1, locks 120 can lock the individual degrees of freedom between two bearings. Specifically, FIG. 6 shows a schematic example of two circular cross-roller bearings 410, 420 as shown in FIG. 4 with bearings 410, 420 connected by rigid connection element 510. FIG. 6 further shows locking element 610 capable of locking the degree of freedom between bearings 410, 420 by means of locking rigid connection element 620, which is rigidly connected to the outer ring of bearing 420, and rigid connection element 510, which is rigidly connected to the inner ring of bearing 420 and thus outer ring of bearing 410.

Control

The robotic device can be envisioned as modular rotational or translational units or building blocks whereby each modular unit represents a degree of freedom. Each unit has its own, where applicable/required/needed, motor, gearbox, electronic board and software to control the respective degree of freedom and measure the position between each combination of two cross roller bearings/units. Reference signals can be sent towards each unit from an external computer device. Communication between units and the main control computer is achieved using a communication system.

Variations

Multiple variations of perpendicular stacking of cross-roller bearings are possible. For practical reasons during bone removal one might prefer to use three cross-roller bearings, i.e. three degrees of freedom, for in-plane (2D) bone milling. Moreover, one might prefer not more than seven degrees of freedom to be able to move in all six degrees of freedom plus one seventh 'redundant' motion be able to avoid collisions with the patient, the robot itself (intra-collisions) and to extend its working range. When using a surgical drilling/milling tool, in most cases five degrees of freedom should suffice, since the orientation of the axisymmetric mill/drill burr is not important. Thus this results in the need to control only five degrees of freedom (assuming no redundancy is required for the task).

What is claimed is:

1. A seven degrees of freedom robotic device for controlling an instrument, comprising:
    (a) a serial kinematic chain of six rotational degrees of freedom and one translational degree of freedom,
        wherein the kinematic chain comprises six circular cross-roller bearings,
        wherein in the kinematic chain each two adjacent circular cross-roller bearings are substantially perpendicularly aligned and connected to each other such that the six circular cross-roller bearings form a stacked serial kinematic chain arrangement,
        wherein each of the circular cross-roller bearings have an inner ring and an outer ring,
        wherein the two adjacent circular cross-roller bearings are rigidly connected to each other through a rigid connection element which connects the inner ring of the first circular cross-roller bearing to the outer ring of the second circular cross-roller bearing in the substantially perpendicularly alignment, the rigid connection element configured to maintain a small distance between the two adjacent circular cross-roller bearings,
        wherein each one of the rotational degrees of freedom is optionally constrained by a locking element thereby reducing the total number of degrees of freedom and providing flexibility and modularity to the robotic device,
        wherein the locking element is configured to lock the degree of freedom of the first circular cross-roller bearing by means of the locking element that is rigidly connected between the rigid connection element and a further rigid connection element, where the further rigid connection element connects the outer ring of the first circular cross-roller bearing to an inner race of a previous, adjacent circular cross-roller bearing of the stacked serial kinematic chain arrangement, the locking element including a lock and a mechanism configured to manually enable or disable the lock, wherein the mechanism configured to manually enable or disable the lock is configured to rotationally decouple the inner ring of the first circular cross-roller bearing from the outer ring of the first circular cross-roller bearing,
wherein the serial kinematic chain is extended by two linear cross-roller bearings adding a translation degree of freedom,
wherein the two linear cross-roller bearings are connected to the inner ring of a top or last circular cross-roller bearing in the chain of six interconnected circular cross-roller bearings; and
(b) an instrument mounted to the two linear cross-roller bearings.

2. The robotic device as set forth in claim 1, wherein the instrument is a surgical instrument or tool.

3. The robotic device as set forth in claim 1, wherein the instrument is a bone-drilling device, a bone-milling device, a 3D printer nozzle or a laser.

4. The robotic device as set forth in claim 1, wherein the substantially perpendicular alignment is defined by 90±5 degrees.

5. The robotic device as set forth in claim 1, further comprising force sensors, torque sensors or a combination thereof.

6. The robotic device as set forth in claim 1, wherein the mechanism configured to manually enable or disable the lock includes a push button.

\* \* \* \* \*